US00PP32654P2

(12) United States Plant Patent
Grazzini

(10) Patent No.: US PP32,654 P2
(45) Date of Patent: Dec. 15, 2020

(54) ***GAILLARDIA* PLANT NAMED 'G15270'**

(50) Latin Name: ***Gaillardia sp.* X *Gaillardia* x *grandiflora***
Varietal Denomination: G15270

(71) Applicant: Richard A. Grazzini, Bellefonte, PA (US)

(72) Inventor: Richard A. Grazzini, Bellefonte, PA (US)

(73) Assignee: GARDENGENETICS LLC, Bellefonte, PA (US)

( * ) Notice: Subject to any disclaimer, the term of this patent is extended or adjusted under 35 U.S.C. 154(b) by 0 days.

(21) Appl. No.: 16/873,537

(22) Filed: Apr. 30, 2020

(30) Foreign Application Priority Data

May 17, 2019 (CA) ..... PBR 19-9868

(51) Int. Cl.
*A01H 5/02* (2018.01)
*A01H 6/14* (2018.01)

(52) U.S. Cl.
USPC ..... Plt./431
CPC ..... *A01H 6/14* (2018.05)

(58) Field of Classification Search
USPC ..... Plt./431
See application file for complete search history.

*Primary Examiner* — Susan McCormick Ewoldt
(74) *Attorney, Agent, or Firm* — C. Anne Whealy

(57) ABSTRACT

A new and distinct cultivar of *Gaillardia* plant named 'G15270', characterized by its upright to outwardly spreading plant habit; vigorous growth habit and moderate growth rate; freely branching habit; dense and bushy habit; strong leaves that resist leaf pathogens; early and freely flowering habit; single sterile inflorescences with bright yellow-colored ray florets; and good garden performance.

1 Drawing Sheet

Botanical designation: *Gaillardia* sp. X *Gaillardia* x *grandiflora*.

Cultivar denomination: 'G15270'.

CROSS-REFERENCE TO A RELATED APPLICATION AND STATEMENT REGARDING PRIOR DISCLOSURES BY INVENTOR/APPLICANT

This application claims priority to a Canadian Plant Breeders' Rights application filed on May 17, 2019, application number 19-9868. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Gaillardia* plant, botanically known as the interspecific hybrid, *Gaillardia* sp. X *Gaillardia* x *grandiflora*, and hereinafter referred to by the name 'G15270'.

The new *Gaillardia* plant is a product of a planned breeding program conducted by the Inventor in Bellefonte, Pa. The objective of the breeding program is to create new sterile *Gaillardia* plants with numerous attractive inflorescences and resistant to pathogens common to *Gaillardia* plants.

The new *Gaillardia* plant originated from a cross-pollination in October, 2014 of a proprietary selection of *Gaillardia* sp. identified as code number G2X-32016-1, not patented, as the female, or seed, parent with a proprietary selection of *Gaillardia* x *grandiflora* identified as code number G2X-32010-2, not patented, as the male, or pollen, parent. The new *Gaillardia* plant was discovered and selected by the Inventor as a single flowering plant from within the progeny of the stated cross-pollination in a controlled environment in Bellefonte, Pa. on Sep. 15, 2015.

Asexual reproduction of the new *Gaillardia* plant by vegetative terminal cuttings in Bellefonte, Pa., since October, 2015 has shown that the unique features of this new *Gaillardia* plant are stable and reproduced true to type in successive generations.

SUMMARY OF THE INVENTION

Plants of the new *Gaillardia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'G15270'. These characteristics in combination distinguish 'G15270' as a new and distinct *Gaillardia* plant:

1. Upright to outwardly spreading plant habit.
2. Vigorous growth habit and moderate growth rate.
3. Freely branching habit; dense and bushy habit.
4. Strong leaves that resist leaf pathogens.

5. Early and freely flowering habit.
6. Single sterile inflorescences with bright yellow-colored ray florets.
7. Good garden performance.

Plants of the new *Gaillardia* differ primarily from plants of the female parent selection in the following characteristics:

1. Plants of the new *Gaillardia* are more vigorous and more outwardly spreading than plants of the female parent selection.
2. Margins of leaves of plants of the new *Gaillardia* are not as deeply dentate as margins of leaves of plants of the female parent selection.
3. Plants of the new *Gaillardia* have single-type inflorescences whereas plants of the female parent selection have double-type inflorescences.
4. Disc florets of plants of the new *Gaillardia* are sterile whereas disc florets of plants of the female parent selection are fertile.

Plants of the new *Gaillardia* differ primarily from plants of the male parent selection in the following characteristics:

1. Plants of the new *Gaillardia* are more vigorous and more outwardly spreading than plants of the male parent selection.
2. Margins of leaves of plants of the new *Gaillardia* are irregularly and shallowly dentate whereas margins of leaves of plants of the male parent selection are entire.
3. Disc florets of plants of the new *Gaillardia* are dark yellow in color whereas disc florets of plants of the male parent selection are deep orange in color.
4. Disc florets of plants of the new *Gaillardia* are sterile whereas disc florets of plants of the male parent selection are fertile.

Plants of the new *Gaillardia* can be compared to plants of *Gaillardia aristata* 'KIEGALYEL', disclosed in U.S. Plant Pat. No. 20,716. In side-by-side comparisons, plants of the new *Gaillardia* differ from plants of 'KIEGALYEL' in the following characteristics:

1. Plants of the new *Gaillardia* are more vigorous than and not as compact as plants of 'KIEGALYEL'.
2. Margins of leaves of plants of the new *Gaillardia* are irregularly and shallowly dentate whereas margins of leaves of plants of 'KIEGALYEL' are mostly entire.
3. Leaves of plants of the new *Gaillardia* are more resistant to leaf pathogens than leaves of plants of 'KIEGALYEL'.
4. Plants of the new *Gaillardia* flower throughout the summer whereas plants of 'KIEGALYEL' typically only flower until mid to late summer in Central Pennsylvania.
5. Disc florets of plants of the new *Gaillardia* are sterile whereas disc florets of plants of 'KIEGALYEL' are fertile.

Plants of the new *Gaillardia* can also be compared to plants of *Gaillardia pulchella* 'DGAL902', disclosed in U.S. Plant Pat. No. 23,833. In side-by-side comparisons, plants of the new *Gaillardia* differ from plants of 'DGAL902' in the following characteristics:

1. Plants of the new *Gaillardia* are more vigorous than and not as compact as plants of 'DGAL902'.
2. Margins of leaves of plants of the new *Gaillardia* are irregularly and shallowly dentate whereas margins of leaves of plants of 'DGAL902' are mostly entire.
3. Leaves of plants of the new *Gaillardia* are more resistant to leaf pathogens than leaves of plants of 'DGAL902'.
4. Plants of the new *Gaillardia* flower throughout the summer whereas plants of 'DGAL902' typically only flower until mid to late summer in Central Pennsylvania.
5. Disc florets of plants of the new *Gaillardia* are sterile whereas disc florets of plants of 'DGAL902' are fertile.

BRIEF DESCRIPTION OF THE PHOTOGRAPHS

The accompanying colored photographs illustrate the overall appearance of the new *Gaillardia* plant showing the colors as true as it is reasonably possible to obtain in colored reproductions of this type. Colors in the photographs may differ slightly from the color values cited in the detailed botanical description which accurately describe the colors of the new *Gaillardia* plant.

At the top of the photographic sheet (FIG. 1) is a side perspective view of a typical flowering plant of 'G15270' grown in a container and at the bottom of the photographic sheet is a close-up view of a typical flowering plant of 'G15270'.

DETAILED BOTANICAL DESCRIPTION

The aforementioned photographs and following observations and measurements describe plants grown during the spring and summer in 15.25-cm containers in a polyethylene-covered greenhouse in St. Thomas, Ontario, Canada and under cultural practices typical of commercial *Gaillardia* production. During the production of the plants, day temperatures averaged 27° C. and night temperatures averaged 15° C. Plants were pinched at planting and were ten weeks from planting rooted cuttings when the photographs and description were taken. In the following description, color references are made to The Royal Horticultural Society Colour Chart, 2007 Edition, except where general terms of ordinary dictionary significance are used.

Botanical classification: *Gaillardia* sp. X *Gaillardia* x *grandiflora* 'G15270'.

Parentage:

*Female, or seed, parent.*—Proprietary selection of *Gaillardia* sp. identified as code number G2X-32016-1, not patented.

*Male, or pollen, parent.*—Proprietary selection of *Gaillardia* x *grandiflora* identified as code number G2X-32010-2, not patented.

Propagation:

*Type.*—Terminal vegetative cuttings.

*Time to initiate roots, summer and winter.*—About two to three weeks at soil temperatures about 22.2° C. and ambient temperatures about 18.3° C.

*Time to produce a rooted young plant from an unrooted cutting, summer and winter.*—About six to eight weeks at soil temperatures about 22.2° C. and ambient temperatures about 18.3° C.

*Root description.*—Medium in thickness, fibrous; typically white to creamy white in color, actual color of the roots is dependent on substrate composition, water quality, fertilizer type and formulation, substrate temperature and physiological age of roots.

*Rooting habit.*—Moderately freely branching, medium density.

Plant description:

*Plant and growth habit*.—Herbaceous perennial; upright to outwardly spreading plant habit; vigorous growth habit and moderate growth rate; freely branching habit with about two to five primary branches each with about twelve secondary branches and each with about four to seven tertiary branches developing per plant; dense and bushy appearance.

*Plant height*.—About 43.2 cm.

*Plant width*.—About 60.3 cm.

*Lateral branch description*.—Length: About 20.2 cm. Diameter: About 3.3 mm. Internode length: About 2.4 cm. Strength: Strong. Aspect: Upright to about 45° from vertical. Texture and luster: Moderately pubescent; matte. Color, developing: Close to 144B. Color, developed: Close to 146C.

*Leaf description*.—Arrangement: Alternate, simple; sessile. Length: About 10.8 cm. Width: About 3 cm. Shape: Oblanceolate. Apex: Mucronate. Base: Sessile, clasping. Margin: Entire or irregularly and shallowly lobed; lobing becoming deeper with development. Texture and luster, upper and lower surfaces: Moderately pubescent; matte. Venation pattern: Pinnate. Color: Developing leaves, upper surface: Close to 138A. Developing leaves, lower surface: Close to 138B. Fully developed leaves, upper surface: Close to 137C; venation, close to 147C. Fully developed leaves, lower surface: Close to 147C; venation, close to 145B.

Inflorescence description:

*Appearance*.—Single inflorescence form with ray and disc florets; inflorescences held mostly upright on strong peduncles; ray and disc florets develop acropetally on a capitulum; inflorescences face upright to outwardly.

*Fragrance*.—Faintly fragrant; sweet and pleasant.

*Flowering response*.—Plants begin flowering about eight weeks after planting; plants flower naturally from late spring until the autumn in Central Pennsylvania.

*Postproduction longevity*.—Inflorescences maintain good substance for about four to six weeks on the plant; inflorescences persistent.

*Quantity of inflorescences*.—Freely flowering habit, about 145 inflorescences develop per plant during the flowering season.

*Inflorescence size*.—Diameter: About 6.9 cm. Height: About 2.1 cm. Disc diameter: About 2.8 cm.

*Receptacles*.—Height: About 4 mm. Diameter: About 6 mm. Color: Close to 155C.

*Inflorescence buds*.—Height: About 9.2 mm. Diameter: About 1.6 cm. Shape: Broadly ovoid. Texture and luster: Pubescent; matte. Color: Close to 147B; immature ray florets, close to 4A.

*Ray florets*.—Quantity per inflorescence: About 16 arranged in about two whorls. Length: About 2.5 cm. Width: About 1.6 cm. Shape: Obovate. Apex: Emarginate or tridentate. Base: Attenuate. Margin: Entire; not undulate. Aspect: Initially, upright to semi-erect and becoming horizontal and reflexed with development. Texture and luster, upper surface: Smooth, glabrous; matte. Texture and luster, lower surface: Sparsely pubescent; matte. Color: When opening, upper surface: Close to 12A; towards the apex, close to 14A to 14B. When opening, lower surface: Close to 12A; towards the apex, close to 14A. Fully opened, upper surface: Close to 12B; towards the apex, close to 14B; venation, similar to lamina; main color becoming closer to 11A with development. Fully opened, lower surface: Close to 12C; towards the apex, close to 14A; venation, close to 145C; with development, color becoming closer to 12D and towards the apex, close to 12B.

*Disc florets*.—Quantity per inflorescence: More than 100 massed at the center of the receptacle in about nine whorls. Length: About 1.2 cm. Diameter: About 2 mm. Shape: Fused tubular. Apex: Acute. Texture and luster, inner and outer surfaces: Pubescent; moderately glossy. Color, inner surface: Apex: Close to 17A. Mid-section: Close to 24B. Base: Close to 145C. Color, outer surface: Apex: Close to 14B. Mid-section: Close to 23C. Base: Close to 145C.

*Involucral bracts*.—Quantity per inflorescence: About 25 to 36 arranged in about four to five whorls. Length: About 1.3 cm. Width: About 4 mm. Shape: Narrowly deltoid. Apex: Long acuminate. Base: Truncate. Margin: Entire, ciliate. Texture and luster, upper and lower surfaces: Pubescent; matte. Color, upper and lower surfaces: Close to 147B.

*Peduncles*.—Length: About 12.6 cm. Diameter: About 1.9 mm. Strength: Strong. Aspect: Upright to semi-upright. Texture and luster: Moderately pubescent; matte. Color: Close to 138B.

*Reproductive organs*.—Androecium: Present on disc florets only. Quantity per floret: Five. Filament length: About 4 mm. Filament color: Close to 155D. Anther length: About 3 mm. Anther shape: Oblong. Anther color: Close to 21A. Pollen amount: Moderate. Pollen color: Close to 23A. Gynoecium: Present on disc florets only. Quantity per floret: One. Pistil length: About 1.1 cm. Stigma diameter: About 1 mm. Stigma shape: Two-lobed. Stigma color: Close to 2D. Style length: About 8 mm. Style color: Close to 2A. Ovary color: Close to 145B.

*Seeds and fruits*.—To date, seed and fruit production have not been observed on plants of the new *Gaillardia* as disc florets of plants of the new *Gaillardia* are sterile.

Pathogen & pest resistance: Plants of the new *Gaillardia* have been observed to tolerate *Gaillardia* Leaf Smut (*Entyloma gaillardianum*). To date, plants of the new *Gaillardia* have not been observed to be resistant to pests and other pathogens common to *Gaillardia* plants.

Garden performance: Plants of the new *Gaillardia* have been observed to have good garden performance and to tolerate wind and rain and temperatures ranging from 13° C. to 38° C.

It is claimed:

1. A new and distinct *Gaillardia* plant named 'G15270' as illustrated and described.

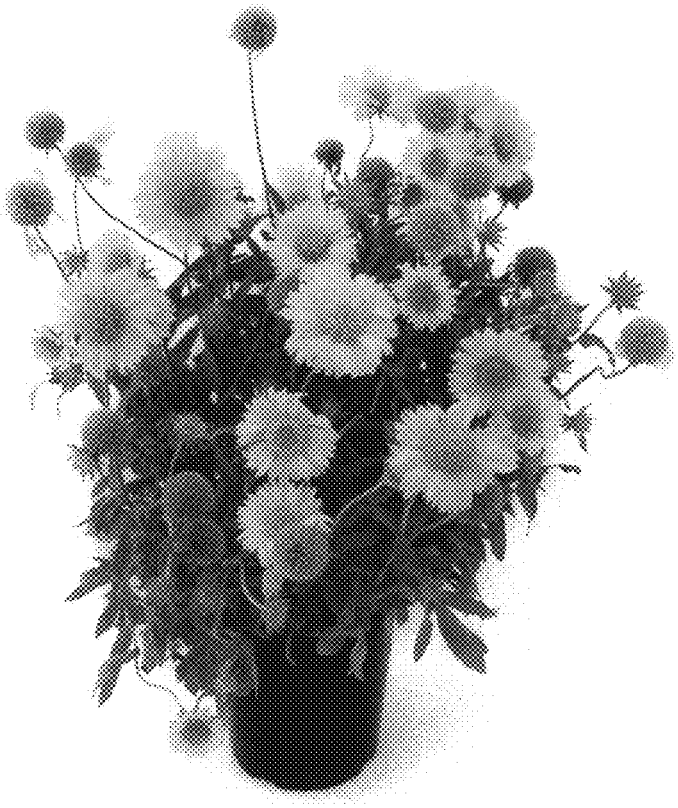
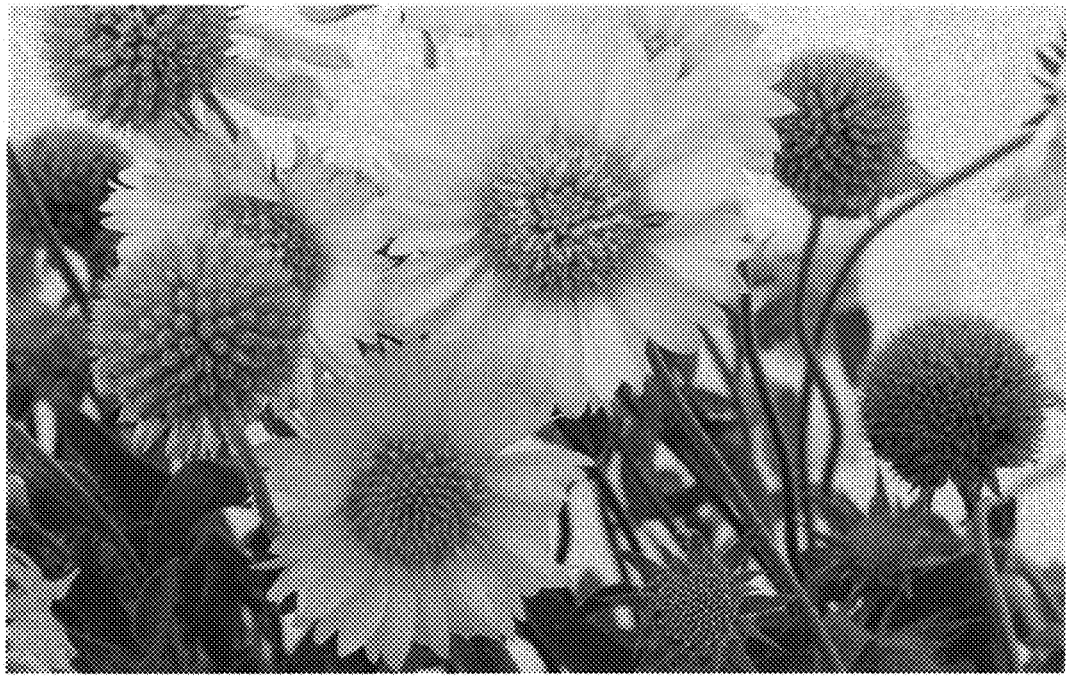

* * * * *